US 11,135,379 B2

(12) United States Patent
Pell et al.

(10) Patent No.: US 11,135,379 B2
(45) Date of Patent: Oct. 5, 2021

(54) METHOD OF DELIVERING PHARMACEUTICAL PRODUCTS

(71) Applicant: BN Intellectual Properties, Inc., Clearwater, FL (US)

(72) Inventors: Donald M. Pell, St. Petersburg, FL (US); Paula Pell, St. Petersburg, FL (US); Michael Spuza, St. Petersburg, FL (US); Govindan Nair, Seminole, FL (US)

(73) Assignee: BN INTELLECTUAL PROPERTIES, INC., Clearwater, FL (US)

( * ) Notice: Subject to any disclaimer, the term of this patent is extended or adjusted under 35 U.S.C. 154(b) by 0 days.

(21) Appl. No.: 16/547,072

(22) Filed: Aug. 21, 2019

(65) Prior Publication Data

US 2020/0261665 A1    Aug. 20, 2020

Related U.S. Application Data

(60) Provisional application No. 62/827,604, filed on Apr. 1, 2019, provisional application No. 62/806,217, filed on Feb. 15, 2019.

(51) Int. Cl.
*A61M 11/00* (2006.01)
*A61K 38/28* (2006.01)
(Continued)

(52) U.S. Cl.
CPC ......... *A61M 11/003* (2014.02); *A24B 15/167* (2016.11); *A24F 47/00* (2013.01);
(Continued)

(58) Field of Classification Search
CPC ...... A61M 11/001–003; A61M 11/005; A61M 16/14–147; A61M 15/0065; A61M 15/0081; A61M 15/0083; A61M 15/0085
See application file for complete search history.

(56) References Cited

U.S. PATENT DOCUMENTS 5,758,637 A * 6/1998 Ivri ...................... A61M 11/005
128/200.14
5,910,301 A 6/1999 Farr et al.
(Continued)

FOREIGN PATENT DOCUMENTS

CN    103285474 A    9/2013
WO    2012064892 A1  5/2012

OTHER PUBLICATIONS

International Search Report and Written Opinion issued in corresponding International Application No. PCT/US2020/029799, dated Jul. 9, 2020, pp. 1-16, U.S. Patent and Trademark Office, Alexandria, VA.

*Primary Examiner* — Valerie L Woodward
(74) *Attorney, Agent, or Firm* — Hauptman Ham, LLP

(57) ABSTRACT

A method of delivering a medication or a pharmaceutical product to a patient includes operations of activating an active mesh of an active mesh nebulizer, the active mesh being in contact with a liquid formulation of the medication, and configured to generate a plume of particles having a particle diameter between 1 and 6 micrometers, directing the plume of particles to a mouth of a patient during an inhalation by a patient; and stopping the plume of particles during the inhalation by the patient such that a substantial majority, or nearly all, of the plume of particles is inhaled by the patient.

22 Claims, 1 Drawing Sheet

(51) Int. Cl.
*A61K 9/00* (2006.01)
*A24F 47/00* (2020.01)
*A24B 15/167* (2020.01)
*A61K 31/4045* (2006.01)

(52) U.S. Cl.
CPC ........ *A61K 9/0078* (2013.01); *A61K 31/4045* (2013.01); *A61K 38/28* (2013.01); *A61M 2202/30* (2013.01); *A61M 2205/0294* (2013.01); *A61M 2205/18* (2013.01); *A61M 2205/50* (2013.01); *A61M 2205/581* (2013.01); *A61M 2205/582* (2013.01); *A61M 2205/583* (2013.01); *A61M 2205/587* (2013.01); *A61M 2230/42* (2013.01)

(56) References Cited

U.S. PATENT DOCUMENTS

| | | | | |
|---|---|---|---|---|
| 7,360,536 | B2* | 4/2008 | Patel | A61M 15/0065 128/200.14 |
| 2003/0159693 | A1* | 8/2003 | Melker | A61M 15/009 128/203.12 |
| 2005/0126562 | A1* | 6/2005 | Rabinowitz | A61M 15/0051 128/200.23 |
| 2006/0067911 | A1* | 3/2006 | Nilsson | A61M 15/0045 424/85.1 |
| 2006/0207591 | A1* | 9/2006 | Gallem | A61M 11/005 128/200.14 |
| 2007/0166336 | A1 | 7/2007 | Delmarre et al. | |
| 2007/0267010 | A1* | 11/2007 | Fink | A61M 11/005 128/200.23 |
| 2008/0060640 | A1* | 3/2008 | Waldner | A61M 15/0085 128/200.16 |
| 2008/0308096 | A1* | 12/2008 | Borgschulte | A61M 11/005 128/200.14 |
| 2010/0282247 | A1* | 11/2010 | Kadrichu | A61K 9/0078 128/200.14 |
| 2012/0322736 | A1 | 12/2012 | Yeomans et al. | |
| 2013/0327323 | A1* | 12/2013 | Rubin | A61M 11/02 128/200.18 |
| 2014/0239525 | A1 | 8/2014 | McConville et al. | |
| 2015/0104506 | A1 | 4/2015 | Hansen et al. | |
| 2016/0310681 | A1* | 10/2016 | Finke | A61M 11/005 |

* cited by examiner

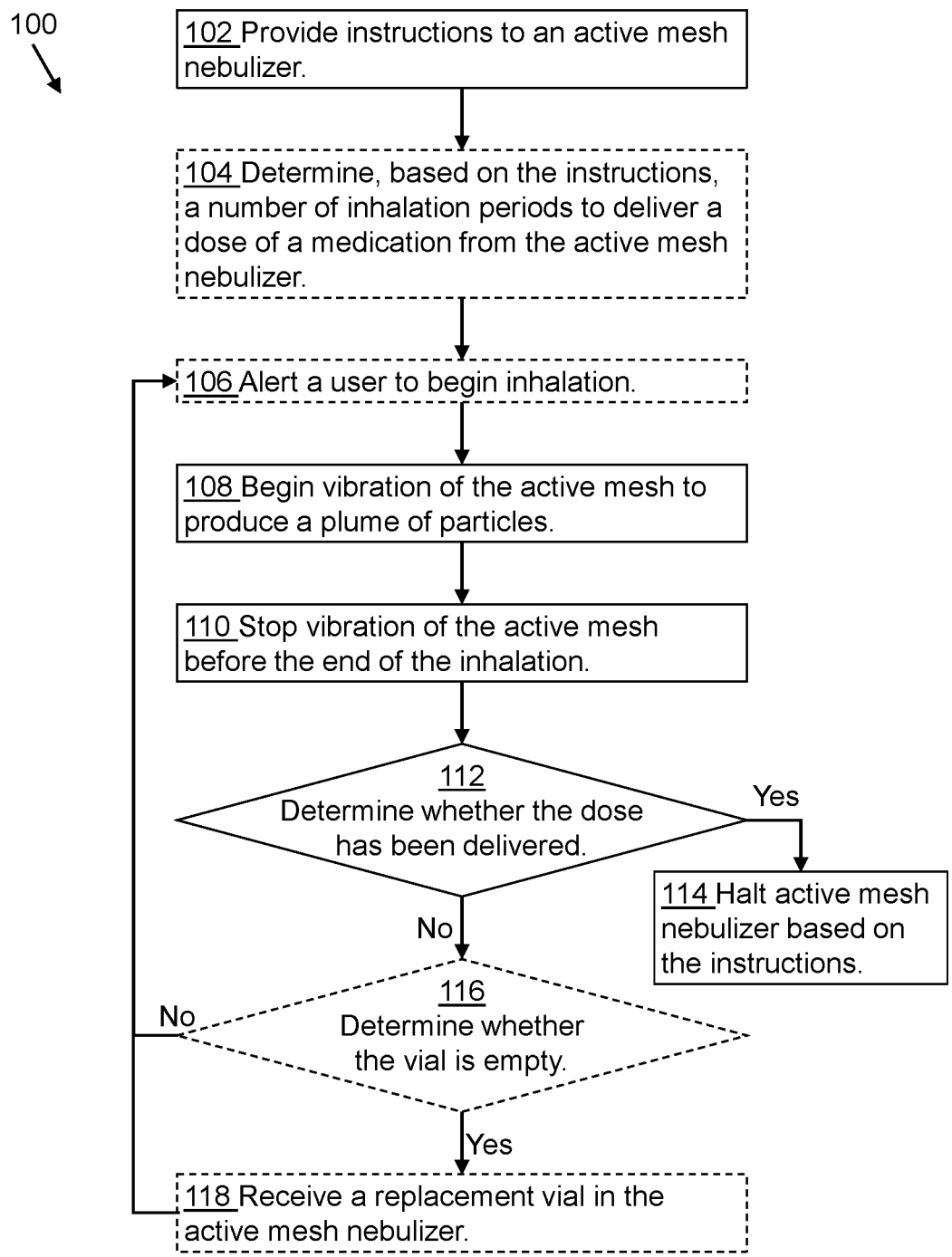

METHOD OF DELIVERING PHARMACEUTICAL PRODUCTS

PRIORITY CLAIM

This application claims priority to, U.S. Patent Application No. 62/806,217, titled "METHOD OF DELIVERING PHARMACEUTICAL PRODUCTS" filed on Feb. 15, 2019, and U.S. Patent Application 62/827,604, titled "NEBULIZER FOR TIME-REGULATED DELIVERY" filed on Apr. 1, 2019, which are incorporated herein by reference.

BACKGROUND

Medical care of patients includes providing accurately dosed pharmaceutical products and medications ("medications") to patients to resolve symptoms of, or to cure, medical conditions. Some medications are incompatible with the gastrointestinal (GI) tract and are delivered by injection, infusion, or transdermal absorption rather than oral delivery. Delivery of some medications by injection or infusion is associated with an elevated risk of infection as the skin is punctured, especially for patients having compromised immune systems.

For patients having certain medical conditions, self-treatment (e.g., self medication) is not feasible because medications appropriate for the medical conditions are difficult to store or administer in a manner indicated by a medical provider, or the medications are prone to abuse by patients. Unauthorized needle re-use is also a potential issue. Some patients are averse to self-treatment by injecting medications, or unable to self-treat because of age or reduced dexterity or strength. Patient self-treatment outside of a medical facility is sometimes irregular with regard to timing or accurate dosing, leading to relapse of symptoms or recurrence of the medical condition/illness.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1 is a flow diagram of a method of delivering medications, in accordance with some embodiments.

DETAILED DESCRIPTION

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. In addition, the present disclosure may repeat reference numerals and/or letters in the various examples. This repetition is for the purpose of simplicity and clarity and does not in itself dictate a relationship between the various embodiments and/or configurations discussed.

The present disclosure describes methods of effectively delivering medications to patients. The methods described herein are suitable for treatment of a patient by a medical provider, and for self-treatment by a patient. In some embodiments of a method according to an embodiment, there is a reduced risk of overdosing on a medication, as compared to traditional methods of treating patients. In some embodiments, a medical provider treats (or a patient self-treats) medical conditions with smaller total doses of medication, as compared to traditional methods of giving patients medications (e.g., oral delivery (swallowing), or injection). In some embodiments, the method described below relates to rapid uptake of medication without use of needles in order to alleviate symptoms of a medical condition. In some embodiments, the method relates to a method of reducing a likelihood of infection by use of the medication delivery device. In some embodiments, the method is associated with a decreased frequency, and/or greater efficacy, of treatment of an illness or medical condition as compared to treatment plans using, e.g., a FHA inhaler or injection of medication. In some embodiments, the method relates to self-treatment by persons with reduced strength or dexterity. In some embodiments, the method relates to treatment of persons with reduced mental capacity, or of children, or the elderly.

The methods of delivering medications described below relate to the generation of a plume of particles from an active mesh nebulizer, the generation being according to a set of instructions stored in and/or performed by the active mesh nebulizer, and the plume of particles being inhaled by a patient. U.S. Patent Application 62/827,604, titled "NEBULIZER FOR TIME-REGULATED DELIVERY" filed on Apr. 1, 2019 and incorporated herein by reference, describes an active mesh nebulizer suitable for performing the method of delivering medications described below, as well as the characteristics of the plume of particles generated by a suitable active mesh nebulizer for performing the method described herein.

FIG. 1 is a flow diagram of a method 100 of delivering pharmaceutical products (e.g., medications) to a patient, according to one or more embodiments of the present disclosure. Method 100 includes an operation 102, wherein a set of instructions is provided to an active mesh nebulizer. An active mesh nebulizer is a medical device configured to deliver the liquid formulation to a patient as a plume of small particles inhaled into the lungs. In some embodiments, the active mesh nebulizer is configured to deliver the plume of particles to a user for treatment of lung tissue, or absorption into the body through the lungs for treatment of other tissues in a patient. An active mesh nebulizer is configured to receive and nebulize liquid formulations from a vial or capsule containing the liquid formulation of a medication or pharmaceutical product. In some embodiments, the liquid formulation in the vial comprises a single dose of medication. In some embodiments, the liquid formulation in the vial comprises multiple doses of medication. The vial is configured to be replaced with a new vial from time to time. In some embodiments, the vial is replaced with a vial having the same liquid formulation of medication. In some embodiments, the vial is replaced with a vial having a different liquid formulation of medication.

The vial dispenses liquid formulations of medication as an aerosol plume, or a plume of particles, according to the instructions performed by the active mesh nebulizer. Characteristics of plumes of particles consistent with the method described herein are described in U.S. Patent Application 62/827,604 referenced above. In some embodiments, the instructions are stored in a computer memory on the active mesh nebulizer. In some embodiments, the instructions are hard-coded into a computer memory, in a manner similar to "firmware" in general purpose computing devices. In some embodiments, the instructions are inaccessible to a user of the active mesh nebulizer, but are modifiable by a medical provider (doctor, nurse, pharmacist, and so forth) upon changing the type of medication, or the concentration of medication, in the liquid formulation dispensed by the active mesh nebulizer.

The instructions for the active mesh nebulizer relate to parameters associated with operating the active mesh nebulizer to deliver a plume of particles to a patient or user, to determine the total dose of the medication in the liquid formulation for a patient or user's care, and/or the timing associated with operating the active mesh to deliver medications to the patient or user. An active mesh nebulizer has an active mesh, a metal sheet having holes therein and connected to a piezoelectric element. During plume generation, the active mesh is in direct contact with the liquid formulation while a controller starts and stops vibration of the active mesh, or the piezoelectric element connected to the active mesh. Plume generation occurs during mesh vibration, resulting in liquid formulation being forced through the holes in the active mesh and into a volume of air (for example within a mouthpiece) where the particles are positioned for inhalation. By directing the plume of particles toward a patient mouth (e.g., by directing the particles into the mouthpiece volume prior to or during inhalation), the entire volume of generated particles is absorbed into the lungs during inhalation, with no waste. In some embodiments, the active mesh vibration starts after a patient or user inhales, and stops before a patient or user stops the inhalation. In some embodiments, the instructions for the active mesh nebulizer determine a duration of a vibration period during a patient or user inhalation to prevent waste of the liquid formulation in an uninhaled plume of particles.

In an optional operation 104, based on the instructions, the active mesh nebulizer determines a duration of a total vibration period, to deliver a full dose of medication to a patient or user. A full dose of medication is a quantity prescribed for periodic delivery to the patient or user by the medical provider. In some embodiments, according to a concentration of medication (a single compound, or a mixture of multiple compounds) in the liquid formulation, the total vibration period to deliver the full dose of medication to the user is shorter than a duration of a single patient inhalation. The total vibration period to deliver a full dose of medication is based on the characterized nebulization rate of the active mesh, the viscosity of the liquid formulation, the quantity of liquid in contact with the mesh (e.g., the coverage area of the liquid on the active mesh) during mesh vibration, the patient or user lung volume, the lung inflation rate for the patient or user, the absorptive surface area of the lung (which may be compromised by medical conditions such as emphysema), and so forth. During operation of an active mesh nebulizer, nebulization rate is a function of at least the active mesh vibration rate, the diameter and number of holes in the mesh, and the voltage applied to the piezoelectric vibrating element. Droplet formation by the active mesh is a function of the liquid formulation viscosity. In some embodiments, a mesh produces an acceptable plume of particles for inhalation into the lungs for a range of liquid formulation viscosities, and a different active mesh is indicated to produce plumes of particles of liquid formulations having a viscosity outside the range of the initial active mesh performance specification. Mesh coverage area also relates to the rate of plume generation. When an entirety of the active mesh is in contact with a liquid formulation, the nebulization/plume generation rate is greater than during operation of the active mesh having only half of the active mesh in contact with the liquid formulation. Plume generation efficiency, and dosing accuracy, is improved by an active mesh nebulizer configured to promote greater amounts of mesh coverage by the liquid formulation.

In some embodiments, the instructions include a programmed total dose of medication for a patient or user, and the total vibration period is determined by dividing the total dose by the nebulization rate of the active mesh nebulizer. In embodiments of the method where the total vibration period is longer than the inhalation period of which a patient or user is capable (due to, e.g., physiological constraints), or expected of a patient or user (due to, e.g., age of the user, or mental capacity), the total vibration period is divided into smaller sub-dose vibration periods and the total dose of medication is provided to the patient or user over multiple inhalations. In embodiments of the method where the total vibration period is less than the inhalation period of which a patient or user is capable (due to, e.g., physiological constraints), or expected of a patient or user (due to, e.g., age of the user, or mental capacity), the total dose of medication is provided to the patient or user in a single inhalation period.

In an optional operation 106, the patient is alerted to begin inhalation in order to receive a total dose, or a sub-dose, of medication. In some embodiments, the patient alert comprises a vibration of the active mesh nebulizer while the patient or user holds the nebulizer against the patient or user's mouth for inhalation. In some embodiments, the patient alert comprises a sound or tone generated to alert the user to begin inhalation. In some embodiments, the patient alert comprises a visual alert (e.g., a blinking light or visual indicator) to begin inhalation. In some embodiments, the patient alert is provided by the active mesh nebulizer. In some embodiments, the patient alert is provided by a computing device communicatively connected to the active mesh nebulizer to facilitate patient treatment and/or active mesh nebulizer operation. Examples of a computing device communicatively connected to the active mesh nebulizer include a dedicated nebulizer controller unit, a "smartphone," a "feature-rich" phone, a computing tablet, or any other kind of computing device configured with software instructions and a communication channel to communicate with the active mesh nebulizer and interact with the patient or user. In some embodiments, the patient alert comprises at least two of more of a sound, a vibration (tactile alert), or a visual alert of the active mesh nebulizer and/or the connected computing device.

According to theory and belief, a patient inhalation typically ranges from about three (3) seconds to about ten (10) seconds before a patient has inhaled sufficient air to inflate the lungs to a maximum lung volume. While inhalation may occur over timespans ranging from 10 seconds to 20 seconds, the reduced inhalation rate is believed to have an impact on the distribution of inhaled particles in the lungs, and on the absorption rate of the medication. For instance, while long, slow inhalations of up to 20 seconds in duration are possible to patients without coughing or exhalation, such inhalation duration is not expected to produce as fast an effect, or as strong a physiological response, as inhaling an equal volume of air over a shorter inhalation period. In some embodiments, the amount of time a patient or user is able to inhale is influenced by lung volume, bronchial diameter, and so forth. In some embodiments, patient age or mental capacity of a patient is a factor in the amount of time a patient or user is able to inhale, and/or the spacing between inhalation periods. For young patients, or patients with cognitive impairment, inhalation periods to deliver a dose of medication are spaced longer apart than for adults or patients with no cognitive impairment in order to provide the patient an opportunity to prepare for a possible second inhalation period for a multi-inhalation medication delivery scenario. According to some embodiments, the instructions are configured to scale the duration of the inhalation period based on (e.g., approximately proportional to) the patient lung volume, as compared to a patient having no physiological impairment. In some embodiments, instructions to the active mesh nebulizer for determining a total number of inhalation periods of an active mesh nebulizer are adjusted according to the age and gender of the patient or user, the measured lung volume of the patient, the peak flow (during exhalation) measurement of a patient or user, or other physiological factors such as surgical history (e.g., whether portions of the lungs have been removed), heart volume, patient weight, fluid buildup around the heart or lungs, and the like.

Method 100 includes operation 108, wherein the vibration of the active mesh is started to generate the plume of particles for the patient or user. In some embodiments, the instructions include a programmable vibration start delay period between the start of the alert, the halt of the patient alert, or some other factor, and the start of the mesh vibration to generate the plume of particles. The duration of a programmable vibration start delay period ranges from about 1 second to about 3 seconds. Vibration start delay periods shorter than about 1 second are believed more likely to result in wasted plume than for longer delay periods. Vibration start delay periods longer than about 3 seconds are believed to be, for most patients, of such length that the patient has begun inhaling before the plume is generated, to inflate the lungs with air that does not contain particles of liquid formulation of the medication. While some patients are expected to find such vibration start delay periods unacceptable (e.g, uncomfortable or inconvenient), the net result is to merely increase a number of inhalation periods to deliver a full dose of medication. For patients with cognitive impairment, or young patients, a vibration delay period of about 3 seconds, or longer, is appropriate to accommodate the different response time or concentration the patient or user is able to pay to the treatment process. The vibration start delay period is intended to be programmable by a medical provider or other person monitoring performance of the patient or user such that the patient or user becomes habituated to a customized treatment process adapted to the patient or user's individual ability. Successful adaptation of the patient or user creates an opportunity for patient self-medication for some medications, without constant oversight by a medical provider.

Method 100 includes an operation 110, wherein the vibration of the active mesh is halted to stop generation of the plume of particles. Generating the plume of particles is halted before the patient stops the inhalation in order to avoid wasting the medication in the uninhaled ending portion of the plume of particles. According to some embodiments, the patient is signaled as to the duration of the inhalation period by an alert from the active mesh nebulizer, or a connected computing device, similar to the alerts described above in optional operation 106. In some embodiments, the patient is provided a periodic alert to track or count to indicate continuing plume generation and avoid inadvertent wasting of a last portion of the plume of particles. In some embodiments, the patient is provided an "ending" alert, different from a starting alert, and/or different from a "tracking" or "counting" alert, to indicate that the plume generation has halted. In some embodiments, a patient is provided an alert (a "further inhalation" alert) to indicate that further inhalation periods are upcoming to prepare for additional plume generation. In some embodiments, a patient is provided an alert (a "final" alert) to indicate that the total dose of medication has been delivered and no further inhalations are upcoming until another full dose of medication is scheduled. In some embodiments, the alerts are tones, vibrations, visual alerts, or recorded messages indicating a status of the active mesh nebulizer or a treatment status (a number of sub-doses delivered, a number of sub-doses remaining, an anticipated number of doses remaining in the vial, and so forth). "Coordinating" alerts to guide a patient or user to start, maintain, or halt inhalation around the programmed generation of the plume of particles are customizable according to the patient's ability to process and adhere to a treatment protocol, and are used singly, or in combination, in order to achieve patient compliance with treatment.

In an operation 112, the active mesh nebulizer controller determines whether the dose of medication has been delivered according to the instructions received by the active mesh nebulizer. Upon determining that the total dose of medication has not been delivered, the method proceeds to operation 116. Upon determining that the total dose of medication has been delivered, the method proceeds to operation 114, wherein the active mesh nebulizer is halted based on the instructions. In some embodiments, the active mesh nebulizer operates under a "fixed dosage" model and is halted until a full dose delay period expires, when an additional full dose of medication is delivered from the active mesh nebulizer in one or more inhalations. In "fixed dosage" operation, the halt between treatment by the active mesh nebulizer is complete and no intermediate operation is allowed (see, e.g., partial dosing, or "running" dosing, below). In some embodiments, the active mesh nebulizer operates under a "partial dosage" model and, upon completion of a full dose of medication, is completely halted until a partial dose delay period expires, at which time a the active mesh nebulizer activates to delivery of a partial dose of medication, but not a full dose of medication. In "partial dosage" operation, the nebulizer becomes available for a treatment with a partial dose of medication from the expiration of the partial delay period until the expiration of the full dose delay period, at which point the nebulizer becomes available for treatment with a full dose of medication.

In an embodiment, the active mesh nebulizer operates a "running dosage" model, wherein the active mesh nebulizer remains available for additional treatment with the medication at all times, unless an additional partial or full treatment of medication will exceed a blood serum concentration, or some other physiological threshold, of the medication in the patient or user. As the amount of delivered medication approaches a calculated blood serum concentration (threshold, especially for tissue toxicity or other adverse effect), the nebulizer completely halts operation until such time as the calculated blood serum concentration, or other physiological threshold, will not be exceeded by an additional partial or full dose of medication. A mode of delivery of medications from the active mesh nebulizer is a function of the chemical nature of the medication, the patient's metabolic ability with regard to the medication, and the patient's sensitivity to the medication, among others. The instructions of the nebulizer are configured to account for the aforementioned factors to avoid over dosage or other adverse patient outcomes based on taking the medication.

Method 100 includes operation 116, wherein, upon determining that the total dose of medication has not been delivered, the nebulizer controller determines whether the vial of medication in the active mesh nebulizer is empty (or, contains an amount of liquid below a fill threshold). In some embodiments, the volume of liquid formulation in the via is calculated, monitored, or estimated, by tracking an elapsed mesh vibration time that the active mesh has vibrated since the vial was placed in the active mesh nebulizer. Based on the characterized nebulization rate of the liquid formulation through the active mesh, as described above, the delivered volume and the remaining volume of liquid formulation are monitored to provide treatment to a patient or user. Upon determining that the remaining volume of liquid is sufficient to provide an additional dose, or a sub-dose, of the medication, the operation proceeds to operation 108. In embodiments of the method where a user is provided with an alert begin inhalation, the method proceeds to optional operation 106 before proceeding to operation 108. Upon determining that the remaining volume of liquid formulation in the vial is too low to deliver an additional sub-dose (e.g., the portion of a dose corresponding to a single inhalation, as described above), the method proceeds to operation 118. In operation 118, the nebulizer is fitted with a replacement vial (an additional vial with the same liquid formulation) in order to continue treatment until the total dose of medication is delivered to the patient. Upon completion of operation 118, the method continues to operation 108 (or, to optional operation 106 before proceeding to operation 108).

According to the above-described method, some medical conditions are treated with a dose of medication from a single inhalation from an active mesh nebulizer. In some embodiments, a medical condition is treated with a dose which spans multiple inhalations from an active mesh nebulizer. According to some embodiments, the medications for treating medical conditions are used to target specific tissues, or to create a systemic concentration of medication. According to some embodiments, the medication used in an active mesh nebulizer is suitable for injection, or infusion, but not suitable for oral delivery (e.g., swallowing a capsule, tablet, or liquid) because of incompatibility with the gastrointestinal tract, and/or because of liver toxicity issues. Further description of medications for use in an active mesh nebulizer, and of the benefits of delivery in a plume of particles rather than by injection, infusion, transdermal delivery, sub-lingual delivery, buccal delivery, and/or oral deliver, follow below.

Use of an active mesh nebulizer to target specific tissues for treatment (tissue-targeted treatment), and the instructions suitable for performing tissue-targeted treatment, follows understanding the characteristics of the particles produced by an active mesh nebulizer, the mechanics of inhalation of the particles, and the pattern of blood flow through a patient. Tissues suitable for targeted tissue treatment are tissues "downstream" of the inhaled plume of particles from the active mesh nebulizer, in proximity to the plume of particles. Suitable tissues for targeted tissue treatment include tissues in at least the respiratory tract and lungs, the heart, and the brain.

The particles produced by a suitable active mesh nebulizer have a particle diameter ranging from about 1.5 micrometers (μm, or microns) to about 6 micrometers. Particles are carried into the lungs during inhalation. Because of the small initial diameters, the produced particles entrained by the inhaled air and carried deep into the lungs, making little or no contact with the walls of the mouth, the throat, and the upper portions of the lungs. It is believed that the small particles absorb some water during inhalation. It is further believed that, despite any water absorption during inhalation, the particles are sufficiently small to undergo efficient entry into the alveoli. In the alveoli, particles contact the alveolar walls and are absorbed into the flow of freshly-oxygenated blood returning from the lungs to the heart. On exiting the heart, oxygenated blood divides into two portions: a first portion of about 20% traveling to the brain, and a second portion of about 80% traveling to a remainder of the body.

The lungs are suitable for targeted-tissue treatment because a plume of particles from an active mesh nebulizer is, according to theory and belief, is efficiently distributed into deep reaches of the lungs. Plumes of material produced by other medical devices (e.g., ultrasonic nebulizers, jet nebulizers, and inhalers for spraying solutions or suspensions of medications into the lungs) or electronic-cigarette-type devices produce larger-diameter particles than a suitable active mesh nebulizer, resulting in reduced particle delivery to the deep reaches of the lungs. Electronic-cigarette-type devices heat or boil liquids to deliver a stream of heated gaseous and liquid material into the lungs. Heating medications is contra-indicated because the heating process has a high likelihood of degrading or modifying a medication, reducing effectiveness and potentially introducing undesirable compounds into the body from the thermal degradation or breakdown of the heated medication. An active mesh nebulizer produces a plume of particles without heating or boiling, and no risk of thermal degradation or breakdown. Other medical devices (e.g., ultrasonic nebulizers, jet nebulizers, and inhalers for spraying solutions or suspensions of medications into the lungs) do not produce as small of particles as an active mesh nebulizer, resulting in low-efficiency distribution of medications into the alveoli and lower branches of the lungs, resulting in lower-efficiency absorption (quantity, and rate) of a delivered medication, and reduced-effectiveness of the delivered medication.

Examples of medications suitable for treatment of lung tissue using the active mesh nebulizer plume to penetrate into the respiratory tract include short-acting beta2-agonist bronchodilators such as, albuterol (albuterol sulfate) and levalbuterol tartrate, long-acting beta2-agonist bronchodilators such as indacaterol, salmeterol xinafoate, and olodaterol hydrochloride, corticosteroids such as flunisolide, ciclesonide, fluticasone furoate, mometasone furoate, fluticasone propionate, budesonide, and beclomethasone dopropionate, and anticholinertic compounds such as ipratropium bromide, glycopyrrolate, umeclidinium, tiotropium bromide, and aclidinium bromide. Medications for treatment of lung tissue also include chemotherapy medications directed toward lung cancer.

The heart is a suitable tissue for targeted-tissue treatment because the heart tissue is immediately downstream from the lungs, with a high concentration of delivered medication from the plume of particles. The brain is suitable for targeted-tissue treatment because 20% of the blood flow exiting the heart is directed toward the brain. A medication used to treat a medical condition associated with the heart or brain benefits from near-immediate absorption into the bloodstream upstream from the tissue where the medication is intended to act. Absorption of the medication into the targeted tissue reduces a concentration of the medication downstream from the targeted-tissue, reducing the overall medication load on the rest of the body and reducing side effects of the medication on other tissues or organ systems.

In a non-limiting example, a vasodilator delivered in a plume of particles to a user to address angina, heart or chest pain associated with restricted blood flow through the heart associated with coronary artery disease, is absorbed into the blood flow from the lungs to the heart, and passes through the left atrium, the left ventricle, and is available for entry into the coronary artery within less than 10 seconds from inhalation. The vasodilator is presented to the target tissue at a locally-high concentration while the total dose of medication delivered to the body is low (systemically low). A vasodilator thus presented to heart tissue is suitable for treating angina symptoms while reducing the likelihood of adverse side effects or drug interactions, and avoiding possible desensitization to the vasodilator. Examples of vasodilators suitable for treating angina include nitroglycerine, nitroprusside, and hydralazine, among others.

In a non-limiting example, ethanol, or ethyl alcohol, delivered in a plume of particles to a user to address symptoms of delirium tremens associated with ethanol withdrawal, is suitable for tissue-targeted treatment of delirium tremens because the chemical is absorbed into the blood flow from the lungs to the heart, and about twenty percent (20%) of the delivered chemical is directed toward the brain after exiting the heart, while the remaining about eighty percent (80%) is directed toward a remainder of the body. The ethanol is presented to the targeted tissue at a locally-high concentration, while the remainder of the alcohol is at a low total dose (systemically low). Thus, a locally-high concentration of ethanol in the brain tissue is believed to be absorbed by the brain to allow mitigation of delirium tremens symptoms during ethanol withdrawal while having negligible impact on other tissues or organs, including the liver, kidneys, and so forth. A patient receiving treatment is at reduced risk of liver damage, especially when the patient has cirrhosis or fatty liver disease, while being weaned off of ethanol. Further, diabetic patients receiving treatment are at reduced risk of diabetic shock, or require reduced blood sugar monitoring, during ethanol withdrawal treatment because of the low systemic concentration of ethanol in the body.

In a non-limiting example, nicotine is a brain-binding medication suitable for use in an active mesh nebulizer to treat tobacco withdrawal symptoms. A liquid formulation of nicotine in water delivered to the brain from a plume of particles absorbed by the lungs produces a cessation of nicotine cravings with a locally-high concentration and a low systemic concentration. In a non-limiting example, 0.0007 milligrams of nicotine delivered in a plume of particles produces a nicotine-associated brain response similar to the effect of smoking a cigarette, including nicotine satiety (lack of cravings or desire for more nicotine) in the user.

Medications suitable for targeted-tissue treatment include brain-binding medications because of the propensity for the medications to undergo absorption by the targeted tissue with locally-high concentration, at a low total dose (a systemic low concentration). Some brain-active or brain-binding medications have a hydrophilic portion and a hydrophobic portion (e.g., the medication is amphiphilic, having both hydrophobic and hydrophilic portions or characteristics). Upon theory and belief, active mesh nebulizer delivery of brain-binding medications results in a locally-high concentration of medication in the brain to achieve the therapeutic effect, while a remainder of the medication is dispersed through the body at low concentrations for metabolism by the liver or other cells at systemic low concentrations which do not result in systemic side effects.

Brain binding or brain-active medications include central nervous system depressants (ethanol, and so forth, including opioids), central nervous system stimulants (caffeine, nicotine, amphetamines, and so forth), pain relievers (e.g., opioids [morphine, oxycodone, hydrocodone, Vicodin, and so forth]), opioid antagonists (compound which bind to opioid receptors at higher efficiencies than opioids without triggering nerve receptor activation, including naloxone, naltrexone, buprenorphine, suboxone, and so forth), psychotropic medications, anti-anxiety medications (e.g., lorazepam, chlordiazepoxide, benzodiazepines, and so forth), anti-depressants (e.g., fluoxetine, citalopram, escitalopram, fluvoxamine, paroxetine, sertraline, vortioxetine, valizodone, lithium, and so forth), anti-psychotic medications (including, e.g., clozapine, lurasidone, olanzapine, risperidone, quetiapine, asenapine, aripiprazole, and cariprazine, among others), sumatriptans for, e.g., headache or migraine medications (including naratriptan, zolmitriptan, rizatripta, frovatriptan, eletriptan, and almotriptan, and imitrex), and so forth. With a low systemic concentration of medications from targeted-tissue treatment using an active mesh nebulizer, the systemic side effects of medications are avoided, while still having the anticipated therapeutic effect.

Some embodiments of the method employ medications which are not intended to treat a medical condition affecting a single tissue or system, but are intended to achieve a high systemic concentration while, e.g., bypassing the issues associated with delivery of medications through the gastrointestinal tract, or with injection or infusion of the medication. Delivery of medications using an active mesh nebulizer provides a method of treating patients (a) without risk of infection due to accidental needle sticks, and (b) of treating patients with greater ease and/or convenience, (c) self-treatment by patients with reduced risk of inaccurate dosing/overdosing, and (d) treatment of patients with medications with reduced total dose quantities because active mesh nebulizers allow medical providers to bypass the gastrointestinal tract and avoid the "first pass" effect which reduces the amount of available medication in the blood stream (due to the liver metabolizing medication absorbed into the portal vein from the small intestine before being distributed to the rest of the body).

Medications suitable for use in an active mesh nebulizer to achieve a high systemic level of medication include at least the following: vaccines, insulin, 'biologicals' or 'biosimilars' for treating rejection of transplanted organs, 'biologicals' or 'biosimilars' for treating autoimmune diseases, vitamins for acute deficiency, interferon, chemotherapy agents, methylprednisone, antihistamines, steroids, corticosteroids, hormones, and so forth. Clot-busting medications to dissolve or break down blood clots include at least plasminogen activator (tPA), tenecteplase, alteplase, urokinase, reteplase, and streptokinase.

A common feature of medications is the benefit to the liver of reduced effort to metabolize medications delivered through the gastrointestinal tract, and/or the relatively "large" nature of the therapeutic molecules in the medications (viral and bacterial fragments, or weakened or killed phages, proteins, and so forth). In a non-limiting embodiment, a non-steroidal anti-inflammatory (NSAID) medication such as acetaminophen is known to have issues related to acute and chronic toxicity to the liver when taken in too large of doses. Delivery of acetaminophen to the body by an active mesh nebulizer delivers the medication to the body while bypassing the liver "first pass" effect, reducing the likelihood of acute liver toxicity from acetaminophen while providing therapeutic effect to a patient. While delivery of many of the above-mentioned medications is performed via injection, many patients have low tolerance for injected medications on a recurring basis. Further, the need for a medical provided to deliver an injection or infusion of the majority of the above-mentioned medications increases the time to provide medical care, and the financial burden of such care. Delivery of the medications without injection using an active mesh nebulizer, whether in a single inhaled dose, or over multiple inhaled sub-doses, reduces medical cost and increases practitioner availability to handle greater caseload or provide more detailed-care to patients and/or users.

Aspects of the present disclosure relate to method of delivering a medication, including activating an active mesh of an active mesh nebulizer, the active mesh being in contact with a liquid formulation of the medication, and configured to generate a plume of particles having a particle diameter between 1 and 6 micrometers; directing the plume of particles to a mouth of a patient during an inhalation by a patient; and stopping the plume of particles during the inhalation by the patient. In some embodiments, the method further includes determining whether a full dose of the medication has been delivered to the patient during the inhalation by the patient. In some embodiments, the method further includes halting operation of the active mesh nebulizer after the full dose of the medication has been delivered to the patient. In some embodiments, the method further includes determining whether a vial holding the liquid formulation in the active mesh nebulizer is too empty to provide another dose of medication to the patient. In some embodiments, the method further includes replacing the vial with a replacement vial holding the liquid formulation in the active mesh nebulizer. In some embodiments, the method further includes replacing the vial with a replacement vial holding the liquid formulation in the active mesh nebulizer. In some embodiments, delivering a medication further includes delivering a psychotropic medication. In some embodiments, delivering a medication includes delivering a central nervous system stimulant. In some embodiments, delivering a medication includes delivering a pain reliever medication. In some embodiments, delivering a medication includes delivering an opioid antagonist. In some embodiments, delivering a medication further includes delivering a sumatriptan medication. In some embodiments, delivering a medication further includes delivering an anti-psychotic medication. In some embodiments, delivering a medication further includes delivering a chemotherapy agent. In some embodiments, delivering a medication further includes delivering insulin. In some embodiments, delivering a medication further includes delivering a vaccine. In some embodiments, delivering a medication further includes delivering a steroid. In some embodiments, delivering a medication further includes delivering a hormone. In some embodiments, delivering a medication further includes delivering a clot-busting medication.

Aspects of the present disclosure relate to a method of delivering a medication which includes operations of activating an active mesh of an active mesh nebulizer, the active mesh being in contact with a liquid formulation of the medication, and configured to generate a plume of particles having a particle diameter between 1 and 6 micrometers; retaining the plume of particles in a mouthpiece of the active mesh nebulizer for inhalation by a patient, and stopping the plume of particles during the inhalation by the patient. In some embodiments, delivering a medication further includes delivering a medication which is incompatible with passing through a gastrointestinal tract. In some embodiments the method further includes halting operation of the active mesh nebulizer after a full dose of the medication has been delivered to the patient.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of delivering a medication, comprising:
   calculating, based on a dose of the medication to be delivered to a patient, a volume of a liquid formulation of the medication to be delivered to the patient;
   calculating, based on a property of an active mesh of an active mesh nebulizer, a vibration time of the active mesh of the active mesh nebulizer;
   determining a number of inhalation periods to deliver the dose of the medication to the patient;
   determining a delay period between the inhalation periods;
   generating a plume of particles of the liquid formulation of the medication based on the calculated vibration time of the active mesh by activating the active mesh of an active mesh nebulizer, the active mesh being in contact with the liquid formulation of the medication, wherein in the plume of particles greater than 95% of the particles have a particle diameter between 1 and 6 micrometers;
   directing the plume of particles to a mouth of the patient during an inhalation by the patient;
   stopping generating the plume of particles before an end of the inhalation by the patient;
   determining whether the dose of the medication has been delivered to the patient by
      monitoring a vibration time of the active mesh of the active mesh nebulizer,
      calculating a delivered volume of the liquid formulation of the medication based on a monitored vibration time of the active mesh, and
      determining whether the delivered volume of the liquid formulation of the medication and the volume of the liquid formulation of the medication to be delivered to the patient are the same volume;
   repeating generating the plume of particles and directing the plume of particles to the mouth of the patient during the inhalation by the patient until the dose of medication has been delivered; and
   preventing activating the active mesh of the active mesh nebulizer for the delay period upon delivering the dose of the medication.

2. The method of claim 1, further comprising determining whether a full dose of the medication has been delivered to the patient during the inhalation by the patient.

3. The method of claim 2, further comprising halting operation of the active mesh nebulizer after the full dose of the medication has been delivered to the patient.

4. The method of claim 1, further comprising determining whether a vial holding the liquid formulation in the active mesh nebulizer is too empty to provide another dose of medication to the patient.

5. The method of claim 4, further comprising replacing the vial with a replacement vial holding the liquid formulation in the active mesh nebulizer.

6. The method of claim 1, wherein delivering a medication further comprises delivering a psychotropic medication.

7. The method of claim 1, wherein delivering a medication comprises delivering a central nervous system stimulant.

8. The method of claim 1, wherein delivering a medication comprises delivering a pain reliever medication.

9. The method of claim 1, wherein delivering a medication comprises delivering an opioid antagonist.

10. The method of claim 1, wherein delivering a medication further comprises delivering a sumatriptan medication.

11. The method of claim 1, wherein delivering a medication further comprises delivering an anti-psychotic medication.

12. The method of claim 1, wherein delivering a medication further comprises delivering a chemotherapy agent.

13. The method of claim 1, wherein delivering a medication further comprises delivering insulin.

14. The method of claim 1, wherein delivering a medication further comprises delivering a vaccine.

15. The method of claim 1, wherein delivering a medication further comprises delivering a steroid.

16. The method of claim 1, wherein delivering a medication further comprises delivering a hormone.

17. The method of claim 1, wherein delivering a medication further comprises delivering a clot-busting medication.

18. The method of claim 7, wherein the central nervous system stimulant comprises nicotine.

19. A method of delivering a medication, comprising:
calculating, based on a dose of the medication to be delivered to a patient, a volume of a liquid formulation of the medication to be delivered to the patient;
determining whether the dose of the medication has been delivered by monitoring an elapsed time since delivery of a previous dose of the medication;
determining a time for activating an active mesh of an active mesh nebulizer to deliver the dose of the medication;
dividing the time for activating the active mesh of the active mesh nebulizer into inhalation periods;
determining a delay period between the inhalation periods;
activating the active mesh of the active mesh nebulizer to deliver the dose of the medication upon determining that the dose of medication has not been delivered, the active mesh being in contact with a liquid formulation of the medication, and configured to generate a plume of particles wherein greater than 95% of the particles in the plume of particles have a particle diameter between 1 and 6 micrometers;
retaining the plume of particles in a mouthpiece of the active mesh nebulizer for inhalation by a patient;
stopping generating the plume of particles during the inhalation by the patient;
repeating determining whether the dose of the medication has been delivered, wherein determining whether the dose of the medication has been delivered further comprises
monitoring a vibration time of the active mesh of the active mesh nebulizer,
calculating a delivered volume of the liquid formulation of the medication based on the vibration time of the active mesh, and
determining that the delivered volume of the liquid formulation of the medication and the volume of the liquid formulation of the medication to be delivered to the patient are the same volume;
repeating, upon determining that the dose of the medication has not been delivered,
activating the active mesh to deliver the dose of the medication,
retaining the plume of particles in the mouthpiece for inhalation by a patient, and
stopping the plume of particles during the inhalation by the patient; and
preventing activating the active mesh of the active mesh nebulizer for the delay period upon determining that the dose of medication has been delivered.

20. The method of claim 19, wherein delivering a medication further comprises delivering a medication which is incompatible with passing through a gastrointestinal tract.

21. The method of claim 19, further comprising halting operation of the active mesh nebulizer after a full dose of the medication has been delivered to the patient.

22. The method of claim 19, wherein delivering a medication comprises delivering a central nervous system stimulant wherein the central nervous system stimulant comprises nicotine.

* * * * *